(12) United States Patent
Choi et al.

(10) Patent No.: US 10,337,973 B2
(45) Date of Patent: Jul. 2, 2019

(54) METHOD AND SYSTEM FOR ESTIMATING EMPIRICAL SNOW DEPTH

(71) Applicant: Korea Meteorological Administration, Seoul (KR)

(72) Inventors: Jiwon Choi, Seogwipo-si (KR); Ki-Ho Chang, Seogwipo-si (KR); Eunsil Jung, Seogwipo-si (KR); Jin-Yim Jeong, Seoul (KR); Baek-Jo Kim, Jeju-si (KR)

(73) Assignee: Korea Meteorological Administration, Seoul (KR)

( * ) Notice: Subject to any disclaimer, the term of this patent is extended or adjusted under 35 U.S.C. 154(b) by 91 days.

(21) Appl. No.: 15/358,156

(22) Filed: Nov. 22, 2016

(65) Prior Publication Data

US 2018/0136105 A1 May 17, 2018

(30) Foreign Application Priority Data

Nov. 17, 2016 (KR) .................. 10-2016-0153057

(51) Int. Cl.
*G01N 15/02* (2006.01)
*G01B 11/08* (2006.01)
(Continued)

(52) U.S. Cl.
CPC ......... *G01N 15/0205* (2013.01); *G01B 11/08* (2013.01); *G01B 11/22* (2013.01); *G01N 15/06* (2013.01); *G01N 15/1459* (2013.01); *G01W 1/14* (2013.01); *G01N 2015/0046* (2013.01); *G01N 2015/0693* (2013.01); *G01N 2015/1075* (2013.01); *G01N 2015/1493* (2013.01)

(58) Field of Classification Search
CPC .................. G01N 15/205; G01N 15/0205
See application file for complete search history.

(56) References Cited

U.S. PATENT DOCUMENTS

2013/0205890 A1* 8/2013 Jung ................. G01W 1/14
73/170.17

FOREIGN PATENT DOCUMENTS

KR 10-1487745 B1 1/2015
KR 10-1509108 B1 4/2015
(Continued)

*Primary Examiner* — John E Breene
*Assistant Examiner* — Jeffrey C Morgan
(74) *Attorney, Agent, or Firm* — Revolution IP, PLLC

(57) ABSTRACT

Disclosed is a system for estimating a snow depth including: an optical disdrometer for acquiring information on diameters of snow particles and particle number concentration; a laser snow depth gauge for measuring the height of snow accumulated through a laser beam type sensor to provide an observed stop depth; an estimated snow depth equation calculator for determining an optimal index for the diameters of the snow particles provided by the optical disdrometer, substituting the optimal index for a snow depth calculation equation as a first mathematical equation to calculate a computed snow depth, obtaining correlation between the observed snow depth and the computed snow depth, and calculating a regression equation between the observed snow depth and the computed snow depth as an estimated snow depth equation; and a snow depth estimator for estimating the snow depth on the basis of the estimated snow depth equation, and the first mathematical equation.

6 Claims, 5 Drawing Sheets

(51) Int. Cl.
*G01B 11/22* (2006.01)
*G01N 15/06* (2006.01)
*G01W 1/14* (2006.01)
*G01N 15/14* (2006.01)
G01N 15/00 (2006.01)
G01N 15/10 (2006.01)

(56) References Cited

FOREIGN PATENT DOCUMENTS

| KR | 10-1530261 B1 | 6/2015 |
| KR | 10-1538858 B1 | 7/2015 |

\* cited by examiner

[FIG. 1]
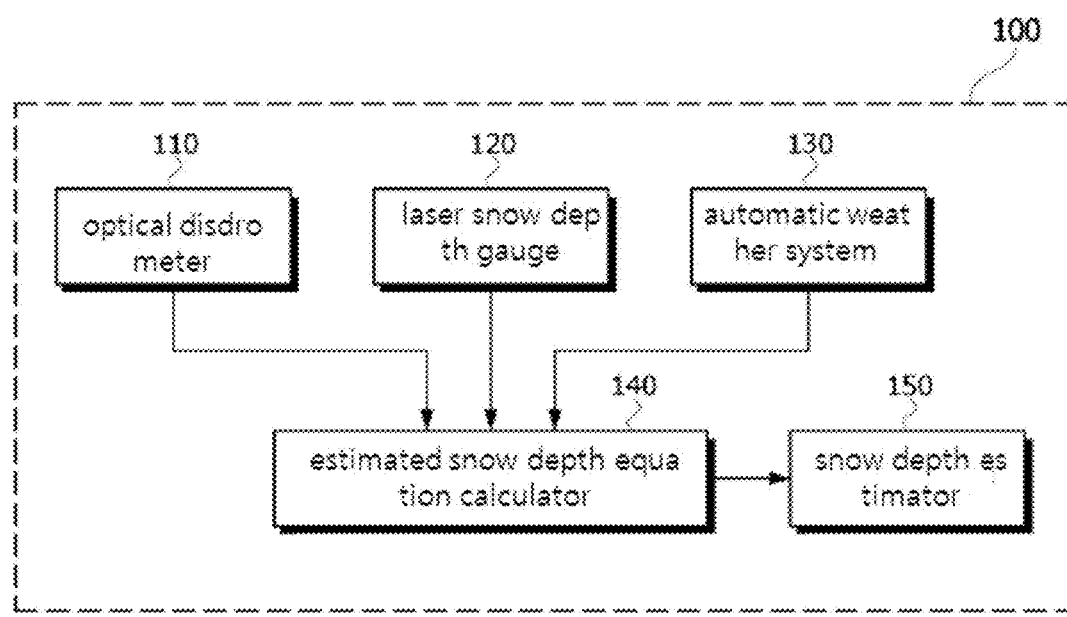

[FIG. 2]
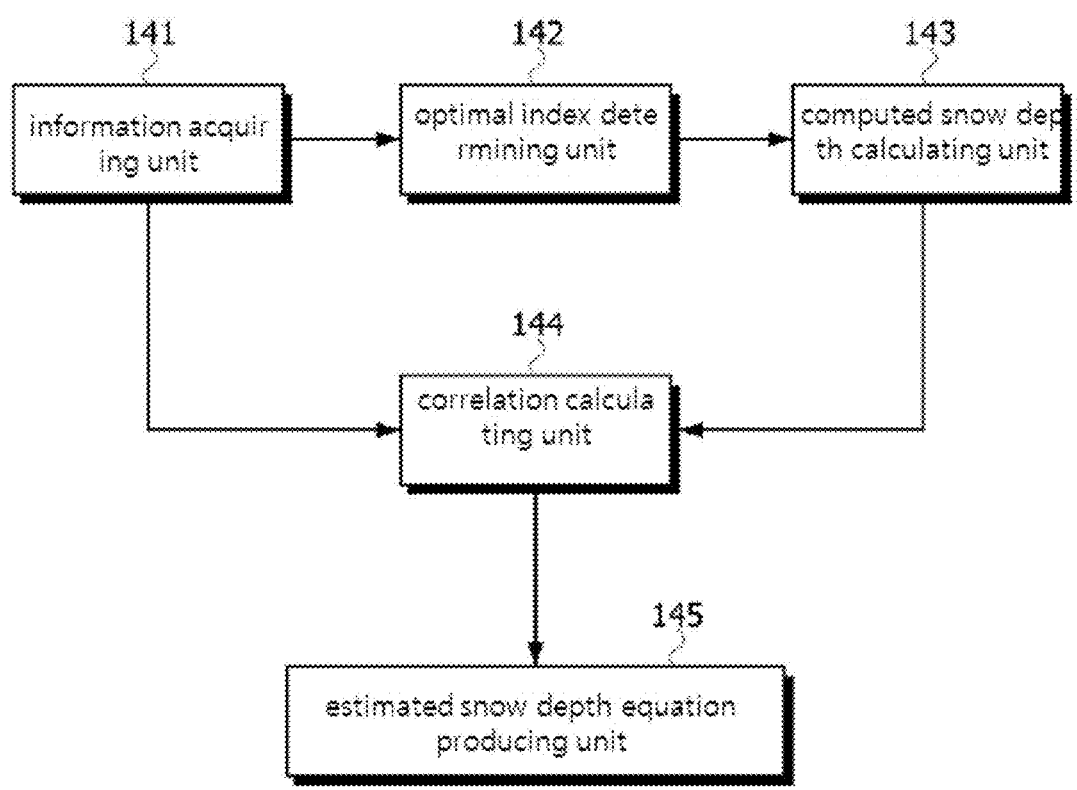

[FIG. 3]
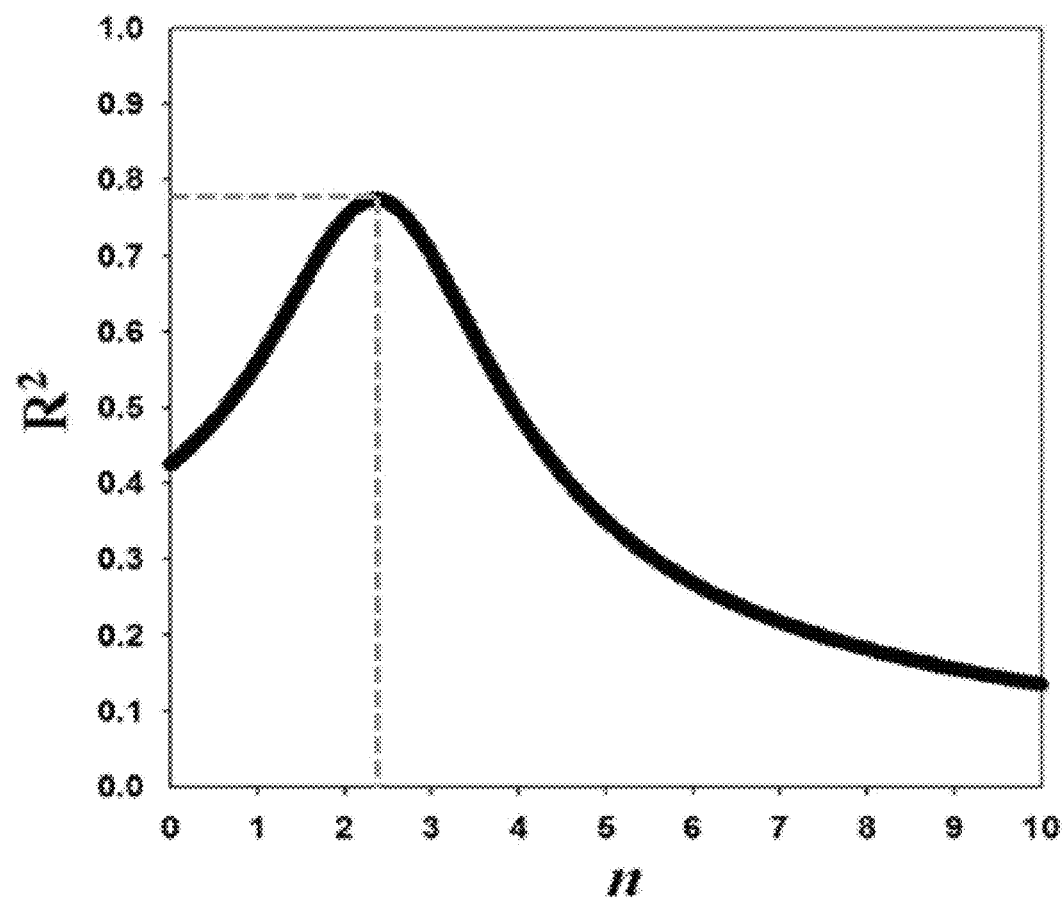

[FIG. 4]
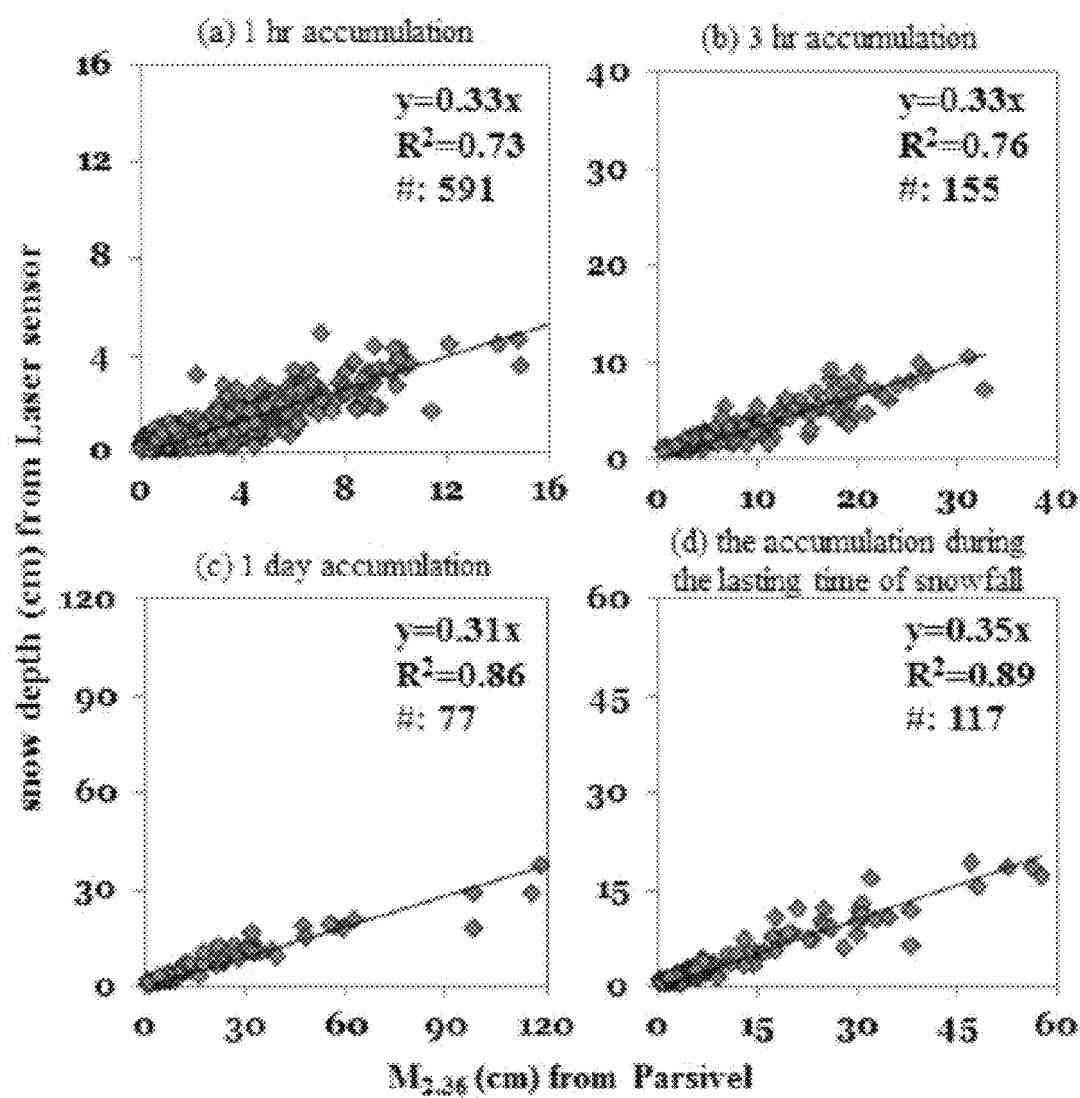

[FIG. 5]
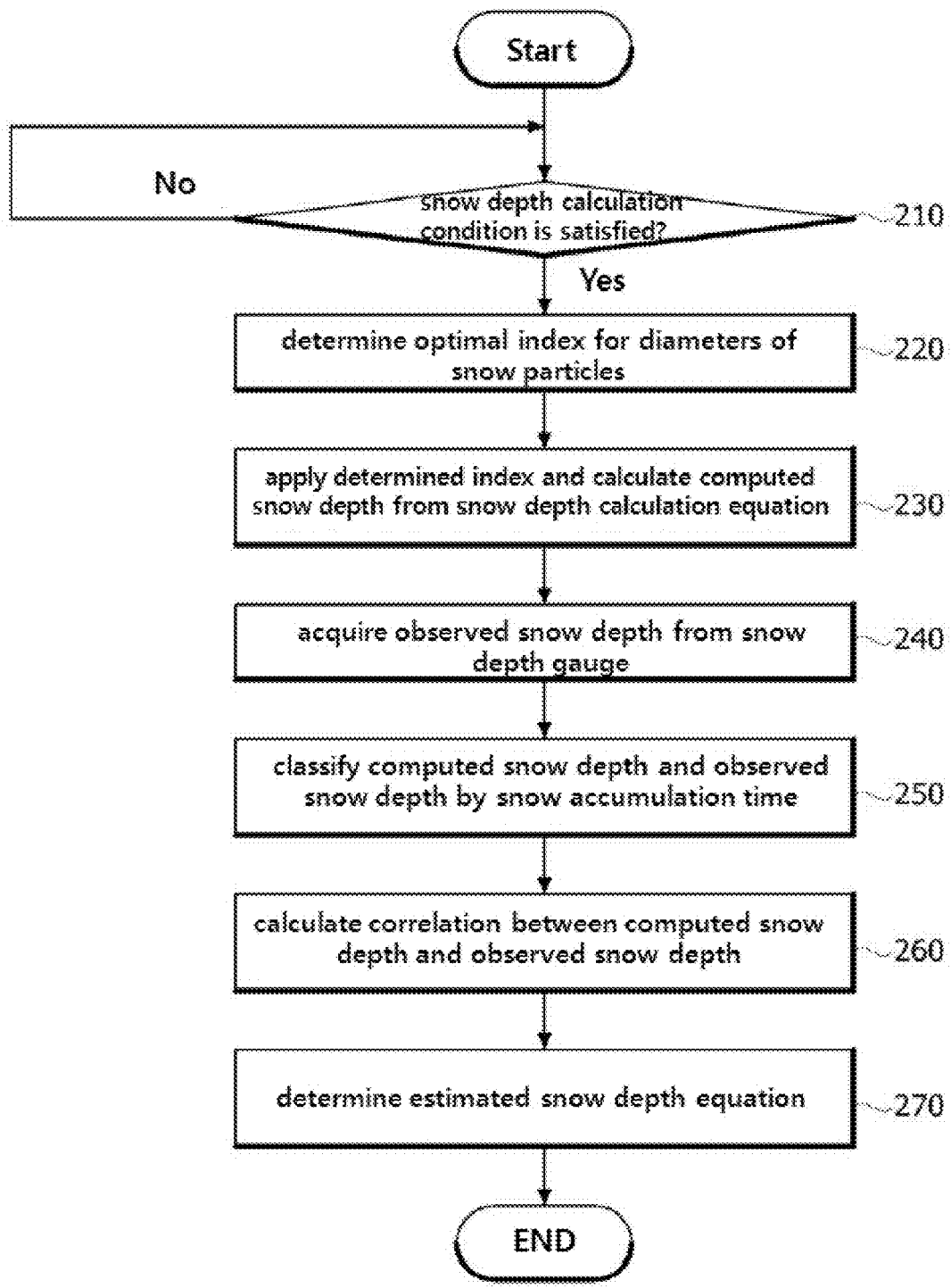

METHOD AND SYSTEM FOR ESTIMATING EMPIRICAL SNOW DEPTH

CROSS REFERENCE TO PRIOR APPLICATIONS

This application claims priority under 35 U.S.C. § 119(a) to Korean Patent Application No. 10-2016-0153057 filed on Nov. 17, 2016, the entire content of which is incorporated herein by reference.

BACKGROUND

The present invention relates to a method and system for estimating a snow depth and, more particularly, to a method and system for estimating an empirical snow depth that makes use of snow particle size distributions.

An observation network is built on a cloud physics observation system of Daegwallyeong in Korea so as to verify snow enhancement experiments, and in this case, a variety of measuring instruments are operated in the observation network. A general object of the snow enhancement is to increase the quantity of snow accumulated on the ground, and the quantity of snow increased by the snow enhancement experiments has been checked in Korea through various observation instruments. Particularly, snow produced by fine particles is accumulated on the ground, which is observed generally by a snow depth gauge. The snow depth gauge serves to measure the snow depth accumulated on a snow measuring plate. Conventional technologies for measuring the snow depth accumulated on the snow measuring plate have been proposed, for example, in Korean Patent No. 10-1530261 entitled "snow depth measuring device and method", Korean Patent No. 10-1509108 entitled "snow depth measuring device and method for operating the same", and Korean Patent No. 10-1538858 entitled "snow depth measuring device".

If the snow depth accumulated on the snow measuring plate is measured, observation errors may occur due to various environmental influences. Since snow is weak in heat, especially, it may melt under the influence of the ground temperature transmitted to the snow measuring plate before accumulated on the ground, and further, snow may fall down due to the influence of wind, thereby causing the observation errors. In addition to the weather factors, besides, the observation errors may occur by animals or plants around the snow measuring plate. Due to the influences of such various factors as mentioned above, accordingly, it is hard to accurately observe the snow depth through the snow depth gauge.

Another method and system for measuring a snow depth is proposed wherein a light emitting element and a light receiving element are accommodated in a scale ruler so that the light emitted from the light emitting element is absorbed to the light receiving element, thereby measuring the snow depth. Such conventional method and system is disclosed, for example, in Korean Patent No. 10-1487745 entitled influence "snow depth measuring device using light source and camera".

Furthermore, a variety of methods and studies have been proposed to observe a snow depth in a more accurate manner. In many countries, accordingly, theoretical equations and empirical equations for estimating a snow depth have been calculated. Since such equations need density observation values, however, they are complicated in computing. So as to remove such complication, accordingly, there is a need to calculate the empirical equation in a simpler manner.

Therefore, there is a definite need for development of a method and system for estimating a snow depth, which is capable of solving the above-mentioned problems, needing no density observation value, and reducing the complication in computing.

SUMMARY

Accordingly, the present invention has been made in view of the above-mentioned problems occurring in the prior art, and it is an object of the present invention to provide a method and system for estimating an empirical snow depth that makes use of snow particle size distributions, while no density observation value is being needed and the complication in computing is being reduced.

To accomplish the above-mentioned object, according to a first aspect of the present invention, there is provided a system for estimating a snow depth including: an optical disdrometer for acquiring information on diameters of snow particles and particle number concentration; a laser snow depth gauge for measuring the height of snow accumulated through a laser beam type sensor to provide an observed snow depth; an estimated snow depth equation calculator for determining an optimal index for the diameters of the snow particles provided by the optical disdrometer, substituting the optimal index for a snow depth calculation equation as a first mathematical equation as indicated below to calculate a computed snow depth, obtaining correlation between the observed snow depth and the computed snow depth, and calculating a regression equation between the observed snow depth and the computed snow depth as an estimated snow depth equation; and a snow depth estimator for estimating the snow depth on the basis of the estimated snow depth equation, and the first mathematical equation, $$M_n = \int_{D_{min}}^{D_{max}} D^n N(D) dD = \sum_{D_i=D_{min}}^{D_{max}} D_i^n N(D_i) \Delta D_i$$

wherein $M_n$ indicates a computed snow depth, $D_{max}$ a maximum diameter size, $D_{min}$ a minimum diameter size, D a diameter per volume, n an index for diameter, and N(D) a particle number concentration by diameter size.

According to the present invention, desirably, the system further includes an automatic weather system for periodically producing weather observation information.

According to the present invention, desirably, the estimated snow depth equation calculator includes: an information acquiring unit for receiving the observed snow depth from the laser snow depth gauge and acquiring the weather information from the automatic weather system; an optimal index determining unit for computing $R^2$ between the computed result value from the first mathematical equation and the observed snow depth and determining, as the optimal index, the index at which the $R^2$ has the highest value; a computed snow depth calculating unit for applying the determined index to the snow depth calculation equation as the first mathematical equation to calculate the computed snow depth; a correlation calculating unit for classifying the computed snow depth and the observed snow depth by snow accumulation time and calculating the correlation between the computed snow depth and the observed snow depth by snow accumulation time; an estimated snow depth equation producing unit for determining a second mathematical equation as the regression equation between the computed snow depth and the observed snow depth by snow accumulation time as the estimated snow depth equation, and the second mathematical equation, Estimated Snow Depth (ESD)=$A \times M_{2.36}$ wherein $M_{2.36}$ is an optimal index obtained through the first mathematical equation, A is an inclination of the regression equation by snow accumulation time, and if the accumulation time is under three hours, A is 0.33, while A is 0.35 if the accumulation time is more than five hours.

To accomplish the above-mentioned object, according to a second aspect of the present invention, there is provided a method for estimating a snow depth including the steps of: acquiring information on diameters of snow particles and particle number concentration; determining an optimal index for the diameters of the snow particles; substituting the optimal index for a snow depth calculation equation as a third mathematical equation as indicated below to calculate a computed snow depth and obtaining correlation between the observed snow depth and the computed snow depth; calculating a regression equation between the observed snow depth and the computed snow depth as an estimated snow depth equation; and estimating the snow depth on the basis of the estimated snow depth equation, and the third mathematical equation, $$M_n = \int_{D_{min}}^{D_{max}} D^n N(D) dD = \sum_{D_i=D_{min}}^{D_{max}} D_i^n N(D_i) \Delta D_i$$

wherein $M_n$ indicates a computed snow depth, $D_{max}$ a maximum diameter size, $D_{min}$ a minimum diameter size, D a diameter per volume, n an index for diameter, and N(D) a particle number concentration by diameter size.

According to the present invention, desirably, the step of determining the optimal index for the diameters of the snow particles includes the steps of computing $R^2$ between the computed result value from the third mathematical equation and the observed snow depth and determining, as the optimal index, the index at which the $R^2$ has the highest value.

According to the present invention, desirably, the estimated snow depth equation is expressed by a fourth mathematical equation, and the fourth mathematical equation, Estimated Snow Depth (ESD)=$A \times M_{2.36}$ wherein $M_{2.36}$ is an optimal index obtained through the first mathematical equation, A is an inclination of the regression equation by snow accumulation time, and if the accumulation time is under three hours, A is 0.33, while A is 0.35 if the accumulation time is more than five hours.

According to the present invention, the method and system for estimating an empirical snow depth makes use of snow particle size distribution, while no density observation value is being needed and the complication in computing is being reduced. Accordingly, the method and system for estimating an empirical snow depth according to the present invention can calculate a snow depth from more accurate measurements of the optical disdrometer, determine the estimated snow depth equation optimized for a snow depth case, and thus estimate the snow depth on the basis of the estimated snow depth equation.

BRIEF DESCRIPTION OF THE DRAWINGS

FIG. 1 is a block diagram showing a system for estimating a snow depth according to the present invention.

FIG. 2 is a block diagram showing an estimated snow depth equation calculator of the system according to the present invention.

FIG. 3 is a graph showing an $R^2$ between $M_n$ and snow depth according to the changes in diameters of snow particles.

FIG. 4 illustrates graphs (a), (b), (c) and (d) showing computed snow depths and observed snow depths by snow accumulation time.

FIG. 5 is a flow chart showing a method for estimating a snow depth according to the present invention.

DETAILED DESCRIPTION

Before the present invention is disclosed and described, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure.

Hereinafter, an explanation on a method and system for estimating an empirical snow depth according to the present invention will be in detail given with reference to the attached drawing. In the description, the same reference numerals in the drawing will be used to describe the same components. If it is determined that the detailed explanation on the well known technology related to the present invention makes the scope of the present invention not clear, the explanation will be avoided for the brevity of the description.

According to the present invention, an empirical equation capable of inducing a snow depth is calculated using an instrument like a disdrometer. The disdrometer measures particle sizes and falling speeds of rain drops or snow during precipitation and thus calculates LWC (Liquid Water Content), rain rate, and reflectivity using the measurements. Unlike water drops (rain drops), ice particles (snow) have a variety of shapes and densities, and so as to estimate a snow depth, accordingly, there is a need to induce a relational equation adequate for the snow depth.

According to the present invention, a PARSIVEL (Particle Size Velocity) disdrometer is provided to acquire information in an optical manner when rain or snow falls during precipitation. According to the present invention, in more detail, the information on the snow particle diameters and water densities measured through the PARSIVEL disdrometer is utilized to calculate a computed snow depth as a result value of an optimal moment equation for the diameters, and correlation between the computed snow depth and the observed snow depth through a snow depth gauge is obtained to calculate an empirical equation, so that snow depths can be estimated later with the information of the PARSIVEL disdrometer, not with the information of the snow depth gauge.

A system 100 for estimating an empirical snow depth according to the present invention is shown in FIG. 1.

FIG. 1 is a block diagram showing the system 100 for estimating a snow depth according to the present invention.

According to the present invention, the system 100 for estimating a snow depth includes an optical disdrometer 110, a laser snow depth gauge 120, an automatic weather system 130, an estimated snow depth equation calculator 140, and a snow depth estimator 150.

The optical disdrometer 110 acquires the information (for example, shape) on a falling object using a laser beam. For example, the optical disdrometer 110 emits a laser beam (of 650 nm), converts the intensities of light cut-off strength by the particles of the falling object into an electrical signal, measures the particle size and fall velocity, and calculates, with the reflectivity induced from the measurements, snow strength, snow particle size (diameter), particle number concentration, fall velocity, distance of vision, snow shape, liquid water content, and the like.

Desirably, the optical disdrometer 110 is a PARSIVEL disdrometer.

The laser snow depth gauge 120 automatically measures the height of snow accumulated through a laser beam type sensor. That is, the laser snow depth gauge 120 senses the surface of snow accumulated from the floor on which snow is not accumulated through the sensor and thus measures the snow depth.

The automatic weather system AWS 130 serves to allow weather observation to be automatically carried out through a computer. In more detail, the automatic weather system 130, which automatically produces weather observation information periodically, is installed on a place to which people do not come near or there is no weather station to acquire weather information. The weather information includes a wind direction, wind speed, atmospheric pressure, humidity, temperature, and amount of precipitation.

The estimated snow depth equation calculator 140 determines an optimal index for the diameters of the snow particles using the diameters of the snow particles calculated by the optical disdrometer 110, obtains correlation between the computed snow depth calculated from the optimal index and the observed snow depth from the laser snow depth gauge 120, calculates an estimated snow depth equation, and thus expects an accurate snow depth.

The snow depth estimator 150 estimates the snow depth from the estimated snow depth equation produced by the estimated snow depth equation calculator 140.

FIG. 2 is a block diagram showing the estimated snow depth equation calculator of the system according to the present invention.

In more detail, the estimated snow depth equation calculator 140 includes an information acquiring unit 141, an optimal index determining unit 142, a computed snow depth calculating unit 143, a correlation calculating unit 144, and an estimated snow depth equation producing unit 145.

First, the information acquiring unit 141 receives the weather information from the automatic weather system 130. The weather information includes wind speed information and air temperature information. Further, the information acquiring unit 141 determines whether a snow depth calculation condition is satisfied or not. In more detail, the information acquiring unit 141 selects the materials by time in which a snow depth is actually observed from days having a daily snow depth of more than 1 cm through the laser snow depth gauge 120. Further, the information acquiring unit 141 selects the days having the wind speed of 5 m/s or under and the air temperature of 0° C. or under from the selected materials so as to reduce the observation error and choose appropriate cases.

That is, the information acquiring unit 141 selects the days having a daily snow depth of more than 1 cm from the materials of the laser snow depth gauge 120, and from the selected days, if the wind speed is 5 m/s or under and the air temperature is 0° C. or under, the information acquiring unit 141 determines that the snow depth calculation condition is satisfied. The snow depth calculation condition is the condition in which the particle observation error of the optical disdrometer 110 is low.

The optimal index determining unit 142 extracts the optimal index for the diameters of the snow particles. So as to extract the optimal index, accordingly, the optimal index determining unit 142 applies the values of indexes n for the diameters to 0 to 10 at intervals of 0.01 in a moment equation as a first mathematical equation as will be discussed below and calculates $R^2$ between the computed snow depth and the observed snow depth.

[First mathematical equation]
$$M_n = \int_{D_{min}}^{D_{max}} D^n N(D)dD = \sum_{D_i=D_{min}}^{D_{max}} D_i^n N(D_i) \Delta D_i$$

In the first mathematical equation, $M_n$ indicates a computed snow depth, $D_{max}$ a maximum diameter size, $D_{min}$ a minimum diameter size, D a diameter per volume, n an index for diameter, and N(D) a particle number concentration by diameter size.

The optimal index determining unit 142 computes $R^2$ between the computed result value from the first mathematical equation and the observed snow depth and determines, as an optimal index, the index at which the $R^2$ has the highest value.

FIG. 3 is a graph showing the $R^2$ between $M_n$ and snow depth according to the changes in diameters n of snow particles.

Referring to FIG. 3, when the index n is 2.34, $R^2$ has an optimal value. In this case, the optimal index is determined as 2.34.

The computed snow depth calculating unit 143 obtains a snow depth calculation equation using the determined optimal index. For example, if the optimal index is $M_{2.36}$, it is substituted for the moment equation as the first mathematical equation, thereby obtaining the snow depth calculation equation like a second mathematical equation as will be described below.

[Second mathematical equation]
$$M_{2.36} = 10^{-5} \times \sum_{D_i=D_{min}}^{D_{max}} D_i^{2.36} N(D_i) \Delta D_i$$

The computed snow depth calculating unit 143 calculates the computed snow depth from the snow depth calculation equation as indicated in the second mathematical equation.

The correlation calculating unit 144 classifies the computed snow depth calculated from the snow depth calculation equation as indicated in the second mathematical equation and the observed snow depth by snow accumulation time, calculates the correlation between the computed snow depth and the observed snow depth by snow accumulation time, and checks the correlation therebetween.

FIG. 4 illustrates graphs (a), (b), (c) and (d) showing the computed snow depths and the observed snow depths by snow accumulation time.

Referring to FIG. 4, the graph (a) shows the scatter plot between the computed snow depth and the observed snow depth in case of one hour accumulation of snowfall, the graph (b) shows the scatter plot therebetween in case of three hour accumulation of snowfall, the graph (c) shows the scatter plot therebetween in case of one day accumulation of snowfall, and the graph (d) shows the scatter plot therebetween in case of the accumulation during the lasting time of snowfall.

The estimated snow depth equation producing unit 145 determines a regression equation between the computed snow depth and the observed snow depth by snow accumulation time as an estimated snow depth ESD equation as a third mathematical equation.

$$\text{Estimated Snow Depth (ESD)} = A \times M_{2.36}$$ [Third mathematical equation]

In the third mathematical equation, $M_{2.36}$ is an optimal index obtained through the first mathematical equation, and A is an inclination of the regression equation by snow accumulation time, wherein if the snow accumulation time is under three hours, A is 0.33, and if the snow accumulation time is more than five hours, A is 0.35.

If such estimated snow depth equation is used, a snow depth can be accurately expected.

For example, the snow depth estimator 150 applies the computed snow depth through the moment equation as the first mathematical equation to which the optimal index is applied to the estimated snow depth equation produced by the estimated snow depth equation calculator 140 to the ESD equation as the third mathematical equation and thus estimates a snow depth.

The estimated snow depth equation allows the snow depth to be estimated later, not on the basis of the laser snow depth gauge, but on the basis of the optical disdrometer. That is, the snow depth can be estimated from the estimated snow depth equation on the basis of the information obtained by the optical disdrometer, instead of the observed snow depth obtained from the laser snow depth gauge.

FIG. 5 is a flow chart showing a method for estimating a snow depth according to the present invention.

Referring to FIG. 5, the estimated snow depth equation calculator 140 determines whether the snow depth calculation condition is satisfied at step 210. In this case, the estimated snow depth equation calculator 140 selects the days having a daily snow depth of more than 1 cm through the laser snow depth gauge 120. Further, the estimated snow depth equation calculator 140 receives the weather information from the automatic weather system 130. The weather information includes wind speed information and air temperature information. The estimated snow depth equation calculator 140 determines whether the wind speed is under 5 m/s and the air temperature is under 0° C. If the wind speed is under 5 m/s and the air temperature is under 0° C. among the days having a daily snow depth of more than 1 cm through the laser snow depth gauge 120, the estimated snow depth equation calculator 140 determines that the snow depth calculation condition is satisfied. The snow depth calculation condition is the condition in which the particle observation error of the optical disdrometer 110 is low.

If the snow depth calculation condition is satisfied, the estimated snow depth equation calculator 140 determines the optimal index according to the diameters of the snow particles at step 220. In more detail, the estimated snow depth equation calculator 140 applies the values of indexes n for the diameters to 0 to 10 at intervals of 0.01 in the moment equation as the first mathematical equation and calculates the $R^2$ between the computed estimation value and the observed snow depth.

The estimated snow depth equation calculator 140 computes the $R^2$ between the computed result value from the first mathematical equation and the observed snow depth, and thus determines, as an optimal index, the index at which the $R^2$ has the highest value.

Next, the estimated snow depth equation calculator 140 applies the determined index to the snow depth calculation equation as indicated by the second mathematical equation at step 230 and calculates the computed snow depth.

Further, the estimated snow depth equation calculator 140 acquires the observed snow depth from, for example, the laser snow depth gauge 120, at step 240.

The estimated snow depth equation calculator 140 at step 250 classifies the computed snow depth calculated from the snow depth calculation equation as indicated in the second mathematical equation and the observed snow depth by snow accumulation time. Next, at step 260, the estimated snow depth equation calculator 140 calculates the correlation between the computed snow depth and the observed snow depth by snow accumulation time and checks the correlation therebetween.

Next, as step 270, the estimated snow depth equation calculator 140 determines a regression equation between the computed snow depth and the observed snow depth by snow accumulation time as the estimated snow depth ESD equation as the third mathematical equation.

If the estimated snow depth equation is used, the snow depth can be accurately expected. In other words, the snow depth can be estimated from the estimated snow depth equation on the basis of the information obtained by the optical disdrometer, instead of the observed snow depth obtained from the laser snow depth gauge.

According to the above-mentioned embodiment of the present invention, for example, snowfall is proposed, but the present invention is not limited thereto. For example, the present invention may be applied in case of rainfall, which is obvious to a person skilled in the art.

Since errors may occur by the above-mentioned characteristics of the snow depth gauge, the system and method for estimating the snow depth according to the present invention utilizes the more accurate measurements of the optical disdrometer and calculates the snow depth. Further, the system and method for estimating the snow depth according to the present invention determines the relational equation optimized for the snow depth cases to calculate the estimated snow depth equation with the observed snow depth through the snow depth gauge and thus estimates the snow depth on the basis of the estimated snow depth equation.

According to the present invention, the method for estimating the snow depth has a form of program commands carried out through various computer means in such a manner as to be recorded in computer readable media. The computer readable media include program commands, data files, or data structures solely or combinedly. The program commands recorded in the media are specially designed and built for the embodiment of the present invention, and otherwise, they may be known to a person skilled in computer software and usable by the person. Examples of the computer readable media include hardware devices configured specially to store and carry out the program commands, such as magnetic media like hard disks, floppy disks and magnetic tapes, optical media like CD-ROM and DVD, magneto-optical media like floptical disks, ROM, RAM, and a flash memory. Examples of the program command include machine codes made by compilers and high-level language codes carried out by a computer through an interpreter. The hardware devices are operated by one or more software modules so as to carry out the operations of the embodiment of the present invention, and vice versa.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A system for estimating a snow depth comprising:
an optical disdrometer for acquiring information on diameters of snow particles and particle number concentration;
a laser snow depth gauge for measuring the height of snow accumulated through a laser beam type sensor to provide an observed snow depth;
an estimated snow depth equation calculator for determining an optimal index for the diameters of the snow particles provided by the optical disdrometer, substituting the optimal index for a snow depth calculation equation as a first mathematical equation as indicated below to calculate a computed snow depth, obtaining correlation between the observed snow depth and the computed snow depth, and calculating a regression equation between the observed snow depth and the computed snow depth as an estimated snow depth equation; and
a snow depth estimator for estimating the snow depth on the basis of the estimated snow depth equation,
and the first mathematical equation, $$M_n = \int_{D_{min}}^{D_{max}} D^n N(D)dD = \sum_{D_i=D_{min}}^{D_{max}} D_i^n N(D_i)\Delta D_i$$

wherein $M_n$ indicates a computed snow depth, $D_{max}$ a maximum diameter size, $D_{min}$ a minimum diameter size, D a diameter per volume, n an index for diameter, and N(D) a particle number concentration by diameter size.

2. The system according to claim 1, further comprising an automatic weather system for periodically producing weather observation information.

3. The system according to claim 2, wherein the estimated snow depth equation calculator comprises:
an information acquiring unit for receiving the observed snow depth from the laser snow depth gauge and acquiring the weather information from the automatic weather system;
an optimal index determining unit for computing $R^2$ between the computed result value from the first mathematical equation and the observed snow depth and determining, as the optimal index, the index at which the $R^2$ has the highest value;
a computed snow depth calculating unit for applying the determined index to the snow depth calculation equation as the first mathematical equation to calculate the computed snow depth;
a correlation calculating unit for classifying the computed snow depth and the observed snow depth by snow accumulation time and calculating the correlation between the computed snow depth and the observed snow depth by snow accumulation time;
an estimated snow depth equation producing unit for determining a second mathematical equation as the regression equation between the computed snow depth and the observed snow depth by snow accumulation time as the estimated snow depth equation,
and the second mathematical equation, Estimated Snow Depth (ESD)=$A \times M_{2.36}$ wherein $M_{2.36}$ is an optimal index obtained through the first mathematical equation, A is an inclination of the regression equation by snow accumulation time, and if the accumulation time is under three hours, A is 0.33, while A is 0.35 if the accumulation time is more than five hours.

4. A method for estimating a snow depth by a system comprising an optical disdrometer, a laser snow depth gauge, an estimated snow depth equation calculator, and a snow depth estimator, the estimated snow depth equation calculator being connected to the optical disdrometer, the laser snow depth gauge, and the snow depth estimator respectively, the method comprising the steps of:
acquiring, by the optical disdrometer, information on diameters of snow particles and particle number concentration and, by the laser snow depth gauge, an observed snow depth;
determining, by the estimated snow depth equation calculator, an optimal index for the diameters of the snow particles provided by the optical disdrometer;
substituting, by the estimated snow depth equation calculator, the optimal index for a snow depth calculation equation as a third mathematical equation to calculate a computed snow depth and obtaining correlation between the observed snow depth and the computed snow depth;
calculating, by the estimated snow depth equation calculator, a regression equation between the observed snow depth and the computed snow depth as an estimated snow depth equation; and
estimating, by the snow depth estimator, the snow depth on the basis of the estimated snow depth equation,
and the third mathematical equation, $$M_n = \int_{D_{min}}^{D_{max}} D^n N(D)dD = \sum_{D_i=D_{min}}^{D_{max}} D_i^n N(D_i)\Delta D_i$$

wherein $M_n$ indicates a computed snow depth, $D_{max}$ a maximum diameter size, $D_{min}$ a minimum diameter size, D a diameter per volume, n an index for diameter, and N(D) a particle number concentration by diameter size.

5. The method according to claim 4, wherein the step of determining the optimal index for the diameters of the snow particles comprises the steps of computing $R^2$ between the computed result value from the third mathematical equation and the observed snow depth and determining, as the optimal index, the index at which the $R^2$ has the highest value.

6. The method according to claim 4, wherein the estimated snow depth equation is expressed by a fourth mathematical equation, and the fourth mathematical equation, Estimated Snow Depth (ESD)=$A \times M_{2.36}$ wherein $M_{2.36}$ is an optimal index obtained through the first mathematical equation, A is an inclination of the regression equation by snow accumulation time, and if the accumulation time is under three hours, A is 0.33, while A is 0.35 if the accumulation time is more than five hours.

* * * * *